United States Patent

Inukai et al.

Patent Number: 5,252,592
Date of Patent: Oct. 12, 1993

[54] TETRAZOLEACETIC ACID DERIVATIVES HAVING ALDOSE REDUCTASE INHIBITORY ACTIVITY

[75] Inventors: Sinji Inukai, Hatano; Mitsuzi Agata, Kanagawa; Kiyoshi Akiba, Kanagawa; Takeo Ohmura, Kanagawa; Yoshihiro Horio, Hatano; Yasuhiro Ootake, Minami-ashigara; Shohei Sawaki, Kanagawa; Masayoshi Goto, Isehara, all of Japan

[73] Assignee: Wakamoto Pharmaceutical Co., Ltd., Tokyo, Japan

[21] Appl. No.: 821,456

[22] Filed: Jan. 16, 1992

[30] Foreign Application Priority Data

Jan. 18, 1991 [JP] Japan .................... 3-16889

[51] Int. Cl.$^5$ .................... A61K 31/41; C07D 257/04
[52] U.S. Cl. .................... 514/381; 548/253
[58] Field of Search .................... 548/253; 514/381

[56] References Cited

U.S. PATENT DOCUMENTS 3,453,285 7/1969 Hayal et al. .................... 548/253

FOREIGN PATENT DOCUMENTS 0035228 2/1981 European Pat. Off. .
0388967 3/1990 European Pat. Off. .

OTHER PUBLICATIONS

Chem. Abstracts, vol. 110, No. 13; 114728p (1989).
C. R. Jacobson et al., "Tetrazolylacetic Acids and Esters," Studies in Tetrazole Chemistry. IV, vol. 21, Mar. 1956, pp. 311–316.

Primary Examiner—Bernard Dentz
Attorney, Agent, or Firm—Burns, Doane, Swecker & Mathis

[57] ABSTRACT

A tetrazoleacetic acid derivative represented by the following general formula (I):

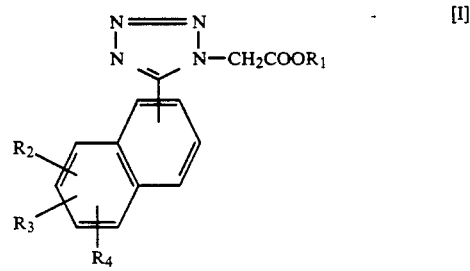

[in Formula (I), $R_1$ represents a hydrogen atom or a lower alkyl group; $R_2$, $R_3$ and $R_4$ are the same or different from each other and are selected from the group consisting of hydrogen, lower alkyl, halogen, lower haloalkyl, hydroxy and lower alkoxy; and tetrazol group is substituted at 1- or 2-position of naphthyl group] except for [5-(1-naphthyl)tetrazol-1-yl]acetic acid and ethyl ester thereof, or a salt thereof.

17 Claims, No Drawings

TETRAZOLEACETIC ACID DERIVATIVES HAVING ALDOSE REDUCTASE INHIBITORY ACTIVITY

BACKGROUND OF THE INVENTION

1. Field of the Invention

The present invention relates to a compound having an aldose reductase inhibitory activity and more specifically to a tetrazoleacetic acid derivative and an aldose reductase inhibitor which comprises the tetrazoleacetic acid derivative as an effective component and which is effective as a preventive medicine and/or remedy for diabetic complications as well as a method for alleviating or reducing diabetic complications.

2. Prior Art

It has been known that aldose reductase inhibitors are effective for prevention and/or treatment of diabetic complications. This is detailed in the article of Dr. Tsuyoshi TANIMOTO [Division of Biological Chemistry and Reference Standards, National Institute of Hygienic Sciences] (see Farumashia, 1988, 24, No.5, pp. 459–463).

This article discloses the chemical structures and 50% inhibitory concentrations ($IC_{50}$) of representative aldose reductase inhibitors such as Alrestatin, Tolrestat, 4-Isopropyl-BPOC, Sorbinil, M-79175, Alconil, ADN-138, Epalrestat, CT-112 and Statil.

The inventors of this invention already conducted screening of novel aldose reductase inhibitors, found that tetrazoleacetic acid derivatives have very high aldose reductase inhibitory activity and already filed two applications for patent (U.S. patent Ser. No. 07/497500 now U.S. Pat. No. 5,055,481 and U.S. patent Ser, No. 07/588,057) now U.S. Pat. No. 5,068,239.

Among these chemical substances according to the present invention, [5-(1-naphthyl)tetrazol-1-yl]acetic acid and ethyl ester there of are reported in an article of C. R. Jakobson et al., J.Org. Chem., vol. 21, P.311, 1956. However, this article only discloses a method for preparing these substance, but there is no disclosure about the biological activity there of.

SUMMARY OF THE INVENTION

An object of the present invention is generally to provide a compound which shows excellent aldose reductase inhibitory activity, has low toxicity to organisms and is quite effective as a preventive medicine and/or remedy for diabetic complications and more specifically to provide a tetrazoleacetic acid derivative.

Another object of the present invention is to provide an aldose reductase inhibitor which comprises the tetrazoleacetic acid derivative as an effective component and which is effective as a preventive medicine and or remedy for diabetic complications.

A further object of the present invention is to provide a method for alleviating or reducing symptoms related to diabetic complications.

According to an aspect of the present invention, there is provided a novel tetrazoleacetic acid derivative represented by the following general formula (I):

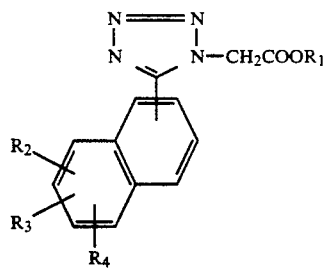

[in Formula (I), $R_1$ represents a hydrogen atom or a lower alkyl group; $R_2$, $R_3$ and $R_4$ are the same or different from each other and are selected from the group consisting of hydrogen, lower alkyl, halogen, lower haloalkyl, hydroxy and lower alkoxy; and tetrazol group is substituted at 1- or 2-position of naphthyl group] except for [5-(1-naphthyl)tetrazol-1-yl]acetic acid and ethyl ester thereof, or a salt thereof.

According to another aspect of the present invention, there is provided an aldose reductase inhibitor which comprises a tetrazoleacetic acid derivative represented by the following general formula (II):

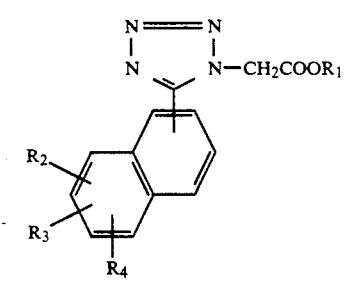

[in Formula (II), $R_1$ represents a hydrogen atom or a lower alkyl group; $R_2$, $R_3$ and $R_4$ are the same or different from each other and are selected from the group consisting of hydrogen, lower alkyl, halogen, lower haloalkyl, hydroxy and lower alkoxy; and tetrazol group is substituted at 1- or 2-position of naphthyl group] or a salt thereof and a pharmaceutical acceptable carrier.

DETAILED EXPLANATION OF THE INVENTION

The tetrazoleacetic acid derivatives and the aldose reductase inhibitor as well as the method for alleviating diabetic complications according to the present invention will hereunder be explained in more detail.

First, each substituent in Formula (I) and (II) will be explained in detail.

The alkyl group represented by $R_1$ is, for instance, methyl, ethyl, propyl, isopropyl, butyl, isobutyl or t-butyl group; the lower alkyl group by $R_2$, $R_3$ or $R_4$ is, for instance, methyl, ethyl, propyl, isopropyl, butyl, isobutyl and t-butyl group; examples of the lower alkoxy group by $R_2$, $R_3$ or $R_4$ are methoxy, ethoxy, propoxy, isopropoxy, butoxy, isobutoxy and t-butoxy groups; the haloalkyl groups by $R_2$, $R_3$ or $R_4$ is for instance, mono-, di- or tri-haloalkyl groups such as chloromethyl, bromomethyl, fluoromethyl and chlorobutyl groups. These substituents may be present on any position on the naphthalene ring.

In addition, salts of the foregoing compounds represented by Formula (I) and (II) wherein $R_1$ is a hydrogen atom are pharmaceutically acceptable ones and typical examples thereof include inorganic salts such as alkali metal salts (for instance, sodium salts and potassium salts), alkaline earth metal salts (for instance, calcium salts and magnesium salts) and ammonium salts; and organic salts such as organic amine salts (for instance, triethylamine salts, pyridine salts and ethanolamine salts) and salts with basic amino acids, for instance, arginine.

The aldose reductase inhibitors according to the present invention comprises, as an essential component, at least one compound represented by the foregoing general formula (II) and are effective as preventive medicines and/or remedies for diabetic complications. It has been known that the term "diabetic complications" means a variety of pathema such as peripheral disorder, retinopathy, naphrosis, cataract and keratopathy. These diseases or disorders are triggered by hyperglycemia resulted from the diabetic disease, that the production of sorbitol in the polyol metabolic pathway is correspondingly abnormally accelerated and that, as a result, a large amount of sorbitol is accumulated within cells. This leads to the onset of these diseases.

The aldose reductase inhibitors of the present invention can suppress the sorbitol-production through strong inhibition of the activity of the aldose reductase which catalyzes the sorbitol-production in the foregoing polyol metabolic pathway and thus show excellent preventive and/or treating effects for these various diabetic complications.

The dose of the compounds of Formula (I) and (II) is appropriately determined depending on the conditions or symptoms of patients to be treated, but in general ranges from 1 to 1,000 mg per day for adult which is administered at one time or over several times The compounds may be administered through any route for medication such as oral administration, subcutaneous injection, intravenous injection and local administration.

The aldose reductase inhibitors of the present invention may usually comprise, in addition to the foregoing compounds as the essential components, pharmaceutically acceptable carriers, vehicles and other additives. The inhibitors of the invention may be used in any dosage form such as tablets, powder, fine particles, granules, capsules, pills, liquid preparations, solution and suspensions for injection and eye drops.

Then methods for preparing the compounds (I) as the essential components, conditions therefor or the like will be detailed below with reference to the following reaction schemes.

Reaction Scheme 1:
Substitution of hydrogen atom for $-CH_2COOR_1$

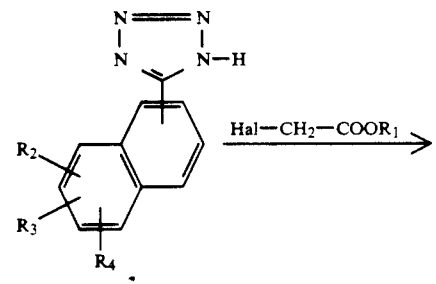

-continued

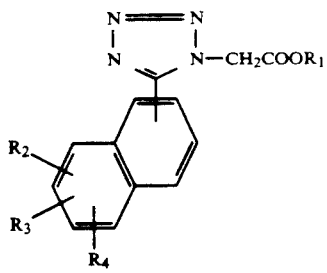

Reaction Scheme 2: Synthesis of tetrazole ring

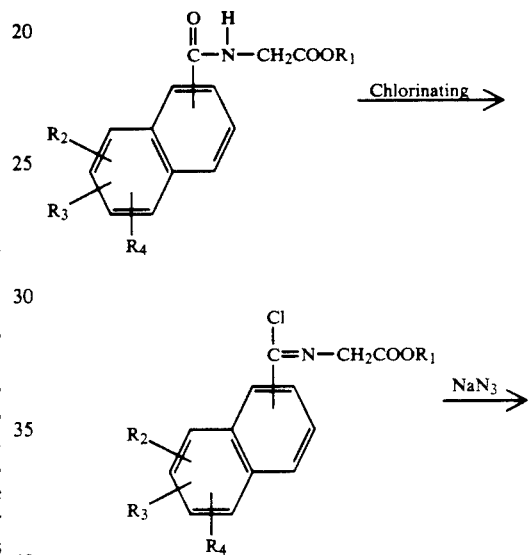

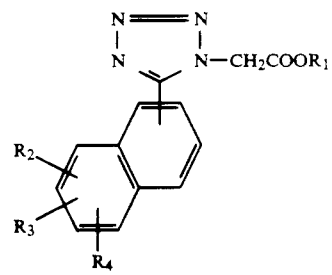

Reaction Scheme 3: Conversion of $R_1$ to hydrogen atom

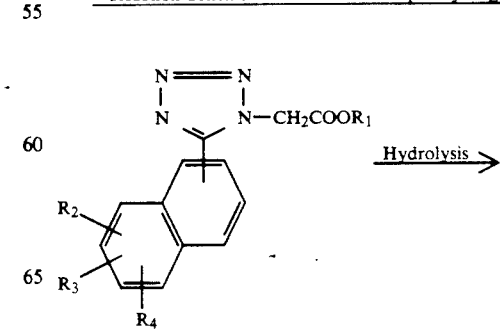

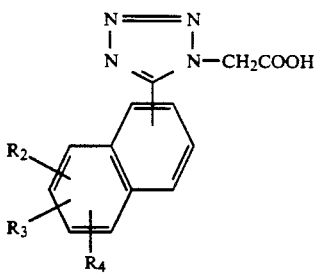

The reaction scheme (1) presents the reaction for the introduction of acetic acid ester to the tetrazole ring, that is, the reaction provides the production method for the intended compounds of the Formula (1) by the reaction of the tetrazole derivatives with halogenoacetate.

In Reaction Scheme 1, the reaction is preferably conducted in a solvent such as methanol, ethanol or propanol at the boiling point of the solvent, in which a base such as sodium hydroxide, potassium hydroxide or potassium carbonate is dissolved.

Reaction Scheme 2 corresponds to a tetrazole cyclization reaction. In this reaction, N-naphthoyl amino alkyl carbonate is reacted with a chlorinating agent such as phosphorus pentachloride, thionyl chloride or thionyl chloride-N,N-dimethyl formamide to produce a corresponding imidoyl chloride, which is them reacted with sodium azide to give the object compound of Formula (1).

The reaction for obtaining the imidoyl chloride can be carried out in an organic solvent such as benzene, toluene or methylene chloride. In general, the reaction is preferably performed at a temperature of not more than room temperature. In the subsequent cyclization reaction, it is preferred to use sodium azide in an amount of 2 to 6 times that of the imidoyl chloride as an intermediate. The cyclization reaction is in general preformed at room temperature in N,N-dimethylformamide.

The reaction scheme 3 means that the compounds of Formula (1) in which $R_1$ is a hydrogen atom may be prepared by hydrolysis of the carboxylic acid ester obtained in the reaction scheme 1 and the reaction scheme 2. The hydrolysis can be performed in the presence of a base such as sodium hydroxide or potassium hydroxide or an acid such as hydrochloric acid, sulfuric acid, acetic acid or trifluoroacetic acid.

The compounds of Formula (I) prepared according to the foregoing method are separated and purified by a chemical operation commonly employed such as extraction, recrystallization and/or column chromatography and the products thus separated and purified are used as essential components for the aldose reductase inhibitors of the present invention.

The present invention will hereinafter described in more detail with reference to the following non-limitative working Examples and the effects practically achieved by the present invention will also be discussed in detail with reference to Test Examples.

EXAMPLE 1

(Reaction Scheme 1)

(1-1) Ethyl[5-[2-(6-methoxy)naphthyl]tetrazol-1-yl]acetate 110 mg of ethyl bromoacetate (0.66 mM) was dropwise added to 10 ml of an ethanol solution containing 100 mg of 5-[2-(6-methoxy)naphthyl]tetrazole (0.44 mM) and 50 mg of triethylamine (0.49 mM) at room temperature. After the completion of the addition, the reaction solution was refluxed for 18 hours and cooled. The reaction solution was concentrated under reduced pressure. The resultant residue was dissolved with chloroform and washed with aqueous solution of sodium hydrogencarbonate and water in order. After washing, the organic phase was dried over with anhydrous magnesium sulfate and then concentrated under reduced pressure. The resultant residue was purified by silica gel chromatography (eluent: benzene/ethylacetate=9/1) to give 20 mg of ethyl[5-[2-(6-methoxy)naphthyl]tetrazol-1-yl]acetate (yield: 14.3%).

M.P. 125.5°–126° C.

N.M.R. (CDCl$_3$) δ: 1.26 (t, 3H, J=7.25 Hz), 3.97 (s, 3H), 4.27 (q, 2H, J=7.25 Hz), 7.19–7.28 (m, 2H), 7.70

(dd, 1H, J=8.50, 2.00 Hz), 7.81 (d, 1H, J=8.50 Hz), 7.89 (d, 1H, J=8.50 Hz), 8.08 (d, H, J=2.00 Hz)

I.R. ν KBr$^{cm-1}$: 3440, 2970, 1750, 1500, 1430

Mass: m/z 312 [M$^+$].

EXAMPLE 2

(Reaction Scheme 2)

(2-1) Methyl[5-(2-naphthyl)tetrazol-1-yl]acetate

Phosphorus pentachloride (190 mg, 0.91 mM) was slowly added to 13 ml of an anhydrous benzene containing 200 mg of N-(2-naphthoyl)glycine methyl ester (0.82 mM) at room temperature. After stirring at room temperature for 30 min., the reaction mixture was evaporated at 40° C. under reduced pressure. The residue was dissolved in 2 ml of N,N-dimethylformamide. The solution was dropwise added to 2 ml of N,N-dimethylformamide suspension containing 140 mg (2.15 mM) of sodium azide at 5° C. to 10° C. while stirring it. After the completion of the addition, the mixture was additionally stirred at room temperature for 30 min. and poured into ice-water. The crystals as precipitated were collected by filtration, washed with water, dried at 60° C. under reduced pressure, and then recrystallized from carbon tetrachloride, to give 156 mg of the object product (yield: 70.7%).

M.P. 97°–98° C.

N.M.R. (CDCl$_3$) δ : 3.97 s, 3H), 5.28 (s, 2H), 7.62–7.72 (m, 3H), 7.92–7.95 (m, 2H), 8.02 (d, 1H, J=8.46

Hz), 8.17 (d, 1H, J=1.21 Hz)

I.R. νKBr$^{cm-1}$: 2950, 1760, 1360, 1220, 1110, 990, 750

Mass: m/z 268 [M+].

The following compounds were prepared in the same manner as Example 2 (2-1).

(2-2) Methyl[5-(1-naphthyl)tetrazol-1-yl]acetate

Yield: 42.8%

Feed material: N-(1-naphthoyl)glycine methyl ester

N.M.R. (CDCl$_3$) δ : 3.68 (s, 3H), 5.04 s, 2H), 7.55–7.64

(m, 5H), 7.95–8.12 (m, 2H)

I.R. νNaCl$^{cm-1}$: 3000, 2950, 1750, 1440, 1220

Mass: m/z 268 [M+].

(2-3) Methyl[5-(1-(6-methoxy-5-trifluoromethyl)naphthyl] tetrazol-1-yl]acetate

Yield: 37.3%

Feed Material: N-[1-(6-methoxy-5-trifluoromethyl) naphthoyl]glycine methyl ester

M.P. 107°–108° C.)

N.M.R. (CDCl$_3$) δ : 3.62 (s, 3H), 3.94 (s, 3H), 4.99 (s,

2H), 7.30 (d, 1H, J=9.67 Hz), 7.39 (d, 1H, J=6.85 Hz), 7.59 (dd, 1H, J=9.27, 6.85 Hz), 7.77 (d, 1H, J=9.27

Hz), 8.38 (d, 1H, J=9.67 Hz)

I.R. ν KBr$^{cm-1}$: 2950, 1760, 1620, 1540, 1430, 1230, 1080,

800

Mass m/z 366 [M+].

(2-4) Ethyl[5-[2-(6-hydroxy)naphthyl]tetrazol-1-yl]acetate

Yield: 62.8%

Feed Material: N-[2-(6-hydroxy)naphthoyl]glycine ethyl ester

M.P. 122°-123° C.

N.M.R. (CDCl$_3$) δ : 1.26 (t, 3H, J=7.15 Hz),4.27(q, 2H, J=7.15

Hz), 5.25 (s, 2H) 6.03 (s, 1H), 7.20–7.26 (m, 2H), 7.63 (dd, 1H, J=8.80, 1.46 Hz), 7.78 (d,2H, J=8.80 Hz), 8.06 (s, 1H)

I.R. νKBr$^{cm-1}$: 3200, 1760, 1640, 1510, 1390, 1200, 1100, 1020, 860

Mass: m/z 298 [M+].

(2-5) Methyl[5-[1-(4-fluoro)naphthyl tetrazol-1-yl]acetate

Yield: 36.5%

Feed Material: N-[1-(4-fluoro)naphthyl]glycine methyl ester

N.M.R. (CDCl$_3$) δ : 3.69 (s, 3H), 5.04 (s, 2H), 7.25–7.32

(m, 1H), 7.55 (dd,1H, J=8.06, 5.13 Hz), 7.61–7.70 (m, 3H), 8.22 (d, 1H, J=7.08 Hz)

I.R. νNaCl$^{cm-1}$: 2950, 1760, 1600, 1540, 1440, 1220, 1050, 1000, 840,770

Mass: m/z 286 [M+].

(2-6) Methyl[5-[1-(2-methyl)naphthyl]tetrazol-1-yl]acetate

Yield: 35.9%

Feed Material: N-[1-(2-methyl)naphthyl]glycine methyl ester

N.M.R. (CDCl$_3$) δ : 2.30 (s, 3H), 3.61 (s, 3H), 4.77 (d, 1H, J=17.46 Hz), 4.98 (d, 1H, J=17.46 Hz), 7.03 (d, 1H,

J=7.57 HZ), 7.43–7.53 (m, 3H), 7.91 (dd, 1H, J=7.57, 1.95

Hz), 7.97 (d, 1H, J=8.54 Hz)

I.R. νNaCl$^{cm-1}$: 3000, 2950, 17960, 1530, 1430, 1360, 1220, 1120, 990, 820, 760

Mass: m/z 282 [M+].

EXAMPLE 3

(Reaction Scheme 3)

(3-1) [5-(2-naphthyl)tetrazol-1-yl acetic acid 30 ml of 2-N sodium hydroxide aqueous solution was added to 5 ml of ethanol solution containing 150 mg (0.56 mM) of methyl[5-(2-naphthyl)tetrazol-1-yl]acetate. The mixture was refluxed for 1 h and cooled. The solution was concentrated under reduced pressure. The resultant residue was dissolved in water. The aqueous solution was acidified with hydrogen chloride, crystals precipitated out were filtered off, washed with water and recrystallized from a 30% ethanol-water mixture to give 85 mg (yield 60%) of the object product.

M.P 180°-181° C. (Decomposition)

N.M.R. (DMSO-d$_6$) δ : 3.30 (bs, 2H), 5.64 (s, 2H), 7.65-7.69 (m, 2H), 7.84 (dd, 1H, J=8.46, 2.02 Hz), 8.03-8.10

(m, 2H) 8.15 (d, 1H, J=8.86 Hz), 8.41 (s, 1H)

I.R. νKBr$^{cm-1}$: 3000, 2950, 1720, 1410, 1220, 810, 760

Mass: m/z 254 [M+].

The following compounds were prepared in the same manner as Example 3 (3-1).

(3-2) [5-(1-naphthyl)tetrazol-1-yl]acetic acid

Yield: 60.5%

Feed Material: Methyl[5-(1-(1-naphthyl)tetrazol-1-yl]acetate

M.P. 223°-224° C. (Decomposition)

N.M.R. (DMSO-d$_6$) δ : 3.34 (s, 3H), 5.32 (s, 2H), 7.57–7.76 (m, 5H), 8.08 - 8.24 (m, 2H)

I.R. δKBr$^{cm-1}$: 3430, 3000, 1730, 1220, 810

Mass: m/z 254 [M+].

(3-3) [5-[2-(6-methoxy)naphthyl]tetrazol-1-yl acetic acid

Yield: 73%

Feed Material: Ethyl[5-[2-(6-methoxy)naphthyl]tetrazol-1-yl]acetate

M.P. 184°-185° C. (Decomposition)

N.M.R. (DMSO-d$_6$) δ : 3.20–4.10 (br, 1H), 3.97 (s, 3H), 5.27 (s, 2H), 7.23–7.27 (m, 2H), 7.73 (d, 1H), J=8.09 Hz), 7.85 (d, 1H, J=8.90 Hz), 7.92 (d, 1H, J=8.90 Hz), 8.14 (s, 1H)

I.R. νKBr$^{cm-1}$: 3410, 1730, 1640, 1500, 1220

Mass: m/z 298 [M+].

(3-4) [5-[1-(6-methoxy-5-trifluoromethyl)naphthyl]tetrazol-1-yl]acetic acid

Yield: 52%

Feed Material: Methyl[5-[1-(6-methoxy-5-trifluoromethyl) naphthyl]tetrazol-1-yl]acetate M.P. 175°-176° C. (Decomposition)

N M.R. (CDCl$_3$) δ : 4.02 (s, 3H), 4.00–4.70 (br, 1H), 5.02 (s, 2H), 7.38 (d, 1H, J=9.16 Hz), 7.53 (d, 1H, J=6.23

Hz), 7.68 (dd, 1H, J=9.52, 6.23 Hz), 7.91 (d, 1H, J=9.52 Hz), 8.44 (d, 1H, J=9.16 Hz)

I.R. νKBr$^{cm-1}$: 2950, 1760, 1620, 1540, 1430

Mass m/z 366 [M+].

(3-5) [5-[2-(6-Hydroxy)naphthyl]tetrazol-1-yl]acetic acid

Yield: 73.6%

Feed Material: Ethyl[5-[2-(6-hydroxy) naphthyl]tetrazol-1-yl]acetate

M.P. 210°-212° C.) Decomposition)

N.M.R. (CDCl$_3$+DMSO-d$_6$) δ : 5.25 (s, 2H), 7.22–7.25 (m,

2H), 7.64 (dd, 1H, J=8.54, 1.46 Hz), 7.79 (dd, 2H, J=8.54

2.68 Hz), 8.09 (s, 1H), 9.57 (br, 1H)

I.R. νKBr$^{cm-1}$: 3300, 2950, 1740, 1620, 1540, 1400, 1230, 1120, 870, 660

Mass: m/z 270 [M+].

(3-6) [5-[1-(4-Fluoro)naphthyl]tetrazol-1-yl]acetic acid

Yield: 87.6%

Feed Material: Methyl[5-[1-(4-fluoro)naphthyl]tetrazol-1-yl]acetate

M.P. 206°-207° C. (Decomposition)

N.M.R. (CDCl$_3$+DMSO-d$_6$) δ : 5.04 (s, 2H), 7.31 (dd, 1H, J=9.89, 8.06 Hz), 7.06–7.70 (m-4H), 8.22 (d, 1H, J=7.32 Hz)

I.R νKBr$^{cm-1}$: 2500, 1740, 1590, 1450, 1220, 840, 770
Mass: m/z 272 [M+].

(3-7) [5-[1-(2-Methyl)naphthyl]tetrazol-1-yl)acetic acid
Yield: 67.0%
Feed Material: Methyl[5-[1-(2-methyl)naphthyl]tetrazol-1-yl]acetate
M.P. 224°–225° C. (Decomposition)
N.M.R. (CDCl$_3$+DMSO-d$_6$) δ : 2.29 (s, 3H), 4.73 (d, 1H, J=15.58 Hz), 4.96 (d, 1H, J=15.58 Hz), 7.05 (d, 1H, J=7.81 Hz), 7.43–74.53 (m, 3H), 7.90–7.93 (m, 1H), 7.99 (d, 1H, J=8.79 Hz)
I.R. νKBr$^{cm-1}$: 3450, 2510, 1930, 1730, 1540, 1440, 1230, 1220, 820
Mass: m/z 268 [M+].

As has been explained above in detail, the aldose reductase inhibitor of the present invention shows excellent aldose reductase inhibitory effect; and has low toxicity. Therefore, it can be used as a medicine for preventing and/or treating mammalian inclusive of man suffering from diabetic complications such as neural disorders, nephrosis, cataract and retinopathy with safety.

The effects and toxicity of the aldose reductase inhibitor according to the present invention will be detailed below with reference to the following Test Examples.

Test Example 1: Test for Examining Aldose Reductase Inhibitory Effect (i) Methodology Six-weeks-old male SD rats were anesthetized with ether and killed. Then their crystalline lenses were immediately removed and stored at −80° C. The lenses were homogenized in 3 volumes of 135 mM sodium potassium phosphate buffer (pH 7.0) and centrifuged at 30,000 rpm for 30 minutes. The resulting supernatant was dialyzed overnight against 0.05M sodium chloride solution to obtain an aldose reductase solution. All operations were conducted at 4° C. and the enzyme solution was stored at −80° C.

The activity of aldose reductase was determined according to a partially modified method of J. H. Kinoshita et al. (J. Biol. Chem., 1965, 240, p. 877). More specifically, 0.1 ml of DL-glyceraldehyde (final concentration: 10 mM) was added to 0.9 ml of 100 mM sodium potassium phosphate buffer (pH 5.2) which contained lithium sulfate (final concentration: 400 mM), reduced nicotinamide adenine dinucleotide phosphate (final concentration: 0.15 mM), the enzyme solution, and the compound to be evaluated (final concentration: 10$^{-6}$M, 10$^{-7}$M or 10$^{-8}$M), and then the reaction was conducted at 30° C. for 5 minutes. During the reaction, the change in the absorbance at 340 nm with time was monitored.

The maximum reducing rate of the absorbance (0) during the reaction was determined. By subtracting, from this value, the maximum reducing rate (U$_0$) at 340 nm of the reaction solution before the addition of the substrate (DL-glyceraldehyde), the reaction rate (V=U−U$_0$) was calculated as a true reaction rate in the presence of the compound to be tested.

The same procedure was repeated except for the absence of the compound to be tested. A true reaction rate (V$_0$) in case the enzyme was not inhibited was calculated (V$_0$=U'−U$_0$'). The aldose reductase inhibitory activity of the test compounds was determined according to the following formula:

Rate of Inhibition (%)=(V$_0$−V)/V$_0$×100

The concentration of inhibitor giving 50% inhibitation of enyzme activity (IC.$_{60}$) was estimated from the least-square regression line of the log dose-response curve.

For comparison, the same tests were conducted using a known aldose reductase inhibitor: ONO-2235 [(E)-3-carboxymethyl-5-[(2E)-methyl-3-phenyl-propenylidene]rhodan].

(ii) Results

The results thus obtained are summarized in the following Table I.

As seen from Table I, the compounds of the present invention tested show aldose reductase inhibitory effect identical to or superior to those attained by the known inhibitor ONO-2235.

TABLE 1

| Compound to be tested (Example No.) | IC$_{50}$ (10$^{-8}$ M) |
| --- | --- |
| 3 - 1 | 5.0 |
| 3 - 2 | 2.5 |
| 3 - 3 | 1.9 |
| 3 - 4 | 13.0 |
| ONO-2235 | 2.2 |

What is claimed is:

1. A tetrazoleacetic acid derivative represented by the following formula (I):

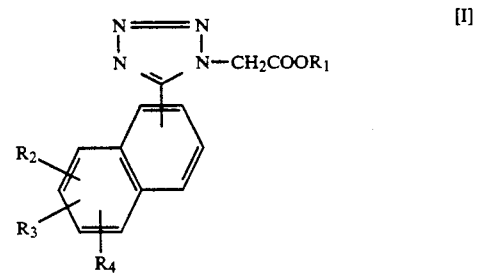

wherein R$_1$ represents a hydrogen atom or a lower alkyl group, R$_2$, R$_3$ and R$_4$ are the same or different and are selected from the group consisting of hydrogen, lower alkyl, halogen, lower haloalkyl, hydroxy and lower alkoxy, the tetrazole group being substituted at the 1- or 2-position of the naphthyl group with the proviso that said derivative is exclusive of [5-(1-naphthyl)tetrazol-1-yl]acetic acid and the ethyl ester thereof, or a salt thereof.

2. The tetrazoleacetic acid derivative of claim 1 wherein, in the general formula (I), the lower alkyl group represented by R$_1$ is a member selected from the group consisting of methyl, ethyl, propyl, isopropyl, butyl, isobutyl and t-butyl group; the lower alkyl group represented by R$_2$, R$_3$ and R$_4$ is a member selected from the group consisting of methyl, ethyl, propyl, isopropyl, butyl, isobutyl, and t-butyl group; the lower alkoxy group is a member selected from the group consisting of methoxy, ethoxy, propoxy, isopropoxy, butoxy, isobutoxy and t-butoxy group; the haloalkyl group is a member selected from the group consisting of mono-, di- and tri-haloalkyl group.

3. The tetrazoleacetic acid derivative of claim 2 wherein the haloalkyl group is a member selected from the group consisting of chloromethyl, bromomethyl, trifluoromethyl and chlorobutyl group.

4. The tetrazoleacetic acid derivative of claim 1 wherein the salt of the compound represented by Formula (I) wherein $R_1$ is a hydrogen atom is a member selected from the group consisting of alkali metal salts, alkaline earth metal salts, ammonium salts, organic amine salts and salts with basic amino acids.

5. The tetrazoleacetic acid derivative of claim 4 wherein the alkali metal salt is a sodium salt or a potassium salt; the alkaline earth metal salt is a calcium salt or a magnesium salt; the organic amine salt is a triethylamine salt, a pyridine salt or an ethanolamine salt; and the basic amino acid salt is an arginine salt.

6. An aldose reductase inhibitor comprising a tetrazoleacetic acid derivative represented by formula (II)

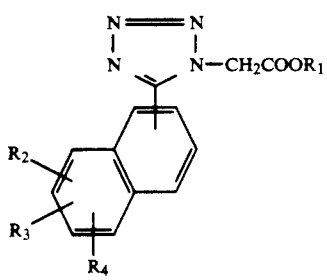

wherein $R_1$ represents a hydrogen atom or a lower alkyl group, $R_2$, $R_3$ and $R_4$ are the same or different and are selected from the group consisting of hydrogen, lower alkyl, halogen, lower haloalkyl, hydroxy and lower alkoxy, the tetrazole group being substituted at the 1- or 2-position of the naphthyl group, or a salt thereof, and a pharmaceutically acceptable carrier.

7. The aldose reductase inhibitor of claim 6 wherein, in the general formula (II), the haloalkyl group is a member selected from the group consisting of chloromethyl, bromomethyl trifluoromethyl and chlorobutyl groups.

8. The aldose reductase inhibitor of claim 6 wherein, in the general formula (II), the lower alkoxy group is a member selected from methoxy, ethoxy, propoxy, isopropoxy, butoxy, isobutoxy and t- butoxy group.

9. The aldose reductase inhibitor of claim 1 wherein the salt of the compound represented by Formula (II) wherein $R_1$ is a hydrogen atom is a member selected from the group consisting of alkali metal salts, alkaline earth metal salts, ammonium salts, organic amine salts and salts with basic amino acids.

10. The aldose reductase inhibitor of claim 9 wherein the alkali metal salt is a sodium salt or a potassium salt; the alkaline earth metal salt is a calcium salt or a magnesium salt; the organic amine salt is a triethylamine salt, a pyridine salt or an ethanolamine salt; and the basic amino acid salt is an arginine salt.

11. A method for treating diabetic complications in an individual in need of such treatment by administering to said individual a therapeutically effective amount of a tetrazoleacetic acid derivative represented by formula (II)

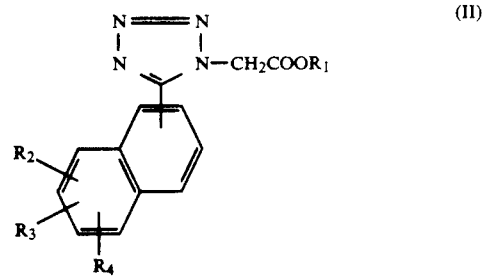

wherein $R_1$ represents a hydrogen atom or a lower alkyl group, $R_2$, $R_3$ and $R_4$ are the same or different and are selected from the group consisting of hydrogen, lower alkyl, halogen, lower haloalkyl, hydroxy and lower alkoxy, the tetrazole group being substituted at the 1- or 2-position of the naphthyl group, or a salt thereof, and a pharmaceutically acceptable carrier.

12. The method of claim 11 wherein, in the general Formula (II) the lower alkyl group represented by $R_1$ is a member selected from the group consisting of methyl, ethyl, propyl, isopropyl, butyl, isobutyl and t-butyl group, the lower alkyl group represented by $R_2$, $R_3$ and $R_4$ is a member selected from the group consisting of methyl, ethyl, propyl, butyl, isopropyl, isobutyl and t-butyl groups; the lower alkoxy group is a member selected from the group consisting of methoxy, ethoxy, propoxy, isopropoxy, butoxy, isobutoxy and t-butoxy; the haloalkyl group is a member selected from the group consisting of mono-, di- and tri-haloalkyl group.

13. The method of claim 12 wherein the haloalkyl group is a member selected from the group consisting of chloromethyl, bromomethyl, trifluoromethyl and chlorobutyl groups.

14. The method of claim 11 wherein the salt of the compound represented by Formula (II) wherein $R_1$ is a hydrogen atom is a member selected from the group consisting of alkali metal salts, alkaline earth metal salts, ammonium salts, organic amine salts and salts with basic amino acids.

15. The method of claim 14 wherein the alkali metal salt is a sodium salt or a potassium salt; the alkaline earth metal salt is a calcium salt or a magnesium salt; the organic amine salt is a triethylamine salt, a pyridine salt or an ethanolamine salt; and the basic amino acid salt is an arginine salt.

16. The method of claim 11 wherein the compound is administered, at one time or over several times, in an amount ranging from 1 to 1,000 mg per day for adult, orally, subcutaneously, intravenously or locally.

17. The method of claim 11 wherein the compound is administered in the form of tablets, powder, fine particles, granules, capsules, pills, liquid preparation, solutions or suspensions for injection or eye drops.

* * * * *